(12) United States Patent
Schoonus-Gerritsma

(10) Patent No.: US 9,925,200 B2
(45) Date of Patent: Mar. 27, 2018

(54) STABLE FORMULATIONS OF TESTOSTERONE UNDECANOATE

(71) Applicant: Merck Sharp & Dohme B.V., Haarlem (NL)

(72) Inventor: Gerritdina G. Schoonus-Gerritsma, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

(21) Appl. No.: 15/317,132

(22) PCT Filed: Jun. 15, 2015

(86) PCT No.: PCT/EP2015/063292
§ 371 (c)(1),
(2) Date: Dec. 8, 2016

(87) PCT Pub. No.: WO2015/193224
PCT Pub. Date: Dec. 23, 2015

(65) Prior Publication Data
US 2017/0136033 A1    May 18, 2017

(30) Foreign Application Priority Data
Jun. 17, 2014    (EP) .................... 14172805

(51) Int. Cl.
A61K 31/568    (2006.01)
A61K 47/14    (2017.01)
A61K 47/10    (2017.01)
A61K 47/44    (2017.01)

(52) U.S. Cl.
CPC ............ *A61K 31/568* (2013.01); *A61K 47/10* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | |
|---|---|---|
| 4,083,973 A | 4/1978 | van der Vies |
| 4,098,802 A | 7/1978 | van der Vies |
| 4,147,783 A | 4/1979 | van der Vies |
| 4,220,599 A | 9/1980 | van der Vies |
| 5,532,002 A | 7/1996 | Story |
| 5,645,856 A | 7/1997 | Lacy et al. |
| 5,738,871 A | 4/1998 | Story |
| 6,652,880 B1 | 11/2003 | Aylwin et al. |
| 7,396,526 B1 * | 7/2008 | Cole ............ A61K 8/365 424/400 |
| 8,241,664 B2 | 8/2012 | Dudley et al. |
| 8,492,369 B2 | 7/2013 | Dudley et al. |
| 8,778,916 B2 | 7/2014 | Dudley et al. |
| 8,778,917 B2 | 7/2014 | Dudley et al. |
| 8,828,428 B1 | 9/2014 | Dudley et al. |
| 2007/0298099 A1 * | 12/2007 | Peresypkin .......... A61K 9/4858 424/456 |
| 2008/0317844 A1 | 12/2008 | Dudley et al. |
| 2011/0160168 A1 * | 6/2011 | Dhingra ................ A61K 9/107 514/170 |
| 2011/0251167 A1 | 10/2011 | Dudley et al. |
| 2012/0135074 A1 | 5/2012 | Chandrashekar et al. |
| 2012/0244215 A1 | 9/2012 | Chandrashekar et al. |
| 2012/0309731 A1 | 12/2012 | Dudley et al. |
| 2013/0022674 A1 | 1/2013 | Dudley et al. |
| 2013/0303495 A1 | 11/2013 | Dhingra et al. |
| 2014/0011789 A1 | 1/2014 | Dudley et al. |
| 2014/0249124 A1 | 9/2014 | Dudley et al. |
| 2014/0274986 A1 | 9/2014 | Dudley et al. |
| 2014/0296199 A1 | 10/2014 | Dudley et al. |
| 2014/0303129 A1 | 10/2014 | Dudley et al. |
| 2015/0343072 A1 | 12/2015 | Dudley et al. |
| 2015/0343073 A1 | 12/2015 | Dudley et al. |
| 2015/0343074 A1 | 12/2015 | Dudley et al. |
| 2016/0000806 A1 | 1/2016 | Dudley et al. |
| 2016/0317553 A1 | 11/2016 | Salameh et al. |

FOREIGN PATENT DOCUMENTS

| | | |
|---|---|---|
| EP | 1189620 B1 | 6/2004 |
| WO | WO1995012383 A1 | 5/1995 |
| WO | WO 95/24893 * | 9/1995 |
| WO | WO1995024893 A1 | 9/1995 |
| WO | WO1997040823 A1 | 11/1997 |
| WO | WO1998036770 A1 | 8/1998 |
| WO | WO1999006024 A1 | 2/1999 |
| WO | WO 00/59482 * | 10/2000 |
| WO | WO2000059482 A1 | 10/2000 |
| WO | WO2000059512 A1 | 10/2000 |
| WO | WO2006113505 A2 | 10/2006 |
| WO | WO2011129812 A1 | 10/2011 |
| WO | WO2015100406 A1 | 7/2015 |

OTHER PUBLICATIONS

Sek et al. in Journal of Pharmacy and Pharmacology 54:29-41 (2002).*
Glycerol Distearate at www.newdruginfo.com/pharmacopeia/bp2003/British%20Pharmacopoeia%20Volume%20I%20and%20II/Monographs%20Medicinal%20and%20Pharmaceutical%20substances/G/Glycerol%20Distearate.htm (retrieved from the internet Sep. 1, 2017).*
Glyceryl monooleate MSDS at www.sciencelab.com/msds.php?msdsId=9924172 (retrieved from the internet Sep. 1, 2017).*
Davidson, D. W. et al., Increasing Circulating androgens with oral testosterone undecanoate in eugonadal men, Chemical Abstracts, 1987, p. 91, vol. 107, No. 13.
Davidson, D. W. et al., Increasing Circulating Androgens With Oral Testosterone Undecanoate in Eugonadal Men, J. Steroid Biochem, 1987, pp. 713-715, vol. 26, No. 6.
Noguchi, T. et al., The effect of drug lipophilicity and lipid vihicles on the lymphatic absorption of various testosterone esters, International Journal of Pharmaceutics, 1985, pp. 173-184, vol. 24.

* cited by examiner

*Primary Examiner* — Dennis Heyer
(74) *Attorney, Agent, or Firm* — Janet E. Fair; Catherine D. Fitch

(57) ABSTRACT

The present invention is directed to stable pharmaceutical formulations. More specifically, the present invention is directed to stable pharmaceutical formulations of testosterone undecanoate.

13 Claims, No Drawings

STABLE FORMULATIONS OF TESTOSTERONE UNDECANOATE

CROSS-REFERENCE TO RELATED APPLICATIONS

This application is a U.S. National Phase application under 35 U.S.C. § 371 of PCT Application No. PCT/EP2015/063292, filed Jun. 15, 2015, which published as WO 2015/193224 A1 on Dec. 23, 2015, and claims priority under 35 U.S.C. § 365(b) from European provisional patent application No. 14172805.5, filed Jun. 17, 2014.

FIELD OF THE INVENTION

The present invention is directed to stable pharmaceutical formulations. More specifically, the present invention is directed to pharmaceutical formulations of testosterone undecanoate resulting in a reduced food effect and increased exposure.

BACKGROUND OF THE INVENTION

Testosterone undecanoate, known as ANDRIOL, has been marketed in many countries for male hypogonadism, since 1978. The first ANDRIOL market formulation was a digestible formulation containing oleic acid. The drawback of this formulation is that it only had a shelf-life of three months at room temperature. The short shelf-life was caused by reesterification of the undecanoate ester with oleic acid. Due to this instability, a new formulation containing castor oil and lauroglycol was developed.

This new formulation is disclosed in U.S. Pat. No. 6,652,880 and US Application No. US2005/0287203 and has been on the market in many countries as ANDRIOL TESTOCAPSS since 2003. The ANDRIOL TESTOCAPS formulation is a non-digestible formulation with a shelf-life of 3 years.

Testosterone undecanoate has a Log P of 9.1 and very low water solubility. Both ANDRIOL and ANDRIOL TESTOCAPS formulations show an absolute bioavailability of 4% in fed state. Together with a medium to high fat meal, testosterone undecanoate is emulgated in the gastrointestinal tract through a combination of digested fats and bile acids. Once emulgated, testosterone undecanoate is incorporated into the chylomicrons and absorbed via the lymph. In fasted state no elevated testosterone undecanoate and/or testosterone serum levels are obtained. Thus, there is still a need for a stable, preferably low-dose pharmaceutical formulation of testosterone undecanoate that results in increased exposure and a decreased food-effect so that patients can rely on testosterone undecanoate being absorbed in fasted state as well as with low-fat meals.

Self-emulsifying formulations of testosterone esters are described in several U.S. patents and applications including: U.S. Pat. No. 8,241,664, which describes a self-emulsifying drug delivery system (SEDDS) of testosterone undecanoate using digestible oils, hydrophilic surfactants, and hydrophobic surfactants; U.S. Patent Application Publication No. 2011/0251167 which describes preparation of SEDDS of testosterone undecanoate containing oleic acid, CREMOPHORE RH40, peppermint oil and borage oil; U.S. Patent Application Publication No. 2012/0135069 which describes preparation of nanonized testosterone esters using solid lipid matrix (stearic acid); U.S. Patent Application 2012/0135074 and 2012/0148675 which describe compositions of testosterone undecanoate in various solubilizers to achieve a concentration of testosterone undecanoate of 14-35% as a solution, mixture of crystalline and solution, and a solid mixture; and U.S. Patent Application No. 20130303495 which describes an emulsion, microemulsion or nanoemulsion formulation for pharmaceutical administration of testosterone undecanoate comprising a digestible lipid, a water-soluble surfactant, a water-insoluble surfactant; a phytosterol and/or phytosterol fatty acid esters, and dl-alpha-tocopherol. However, such formulations do not all achieve a stable, preferably low-dose pharmaceutical formulation of testosterone undecanoate that results in increased exposure and a decreased food-effect so that patients can rely on testosterone undecanoate being absorbed in a fasted state as well as with low-fat meals.

SUMMARY OF THE INVENTION

Since both ANDRIOL and ANDRIOL TESTOCAPS formulations are not capable of self-emulgation in watery systems it is expected these formulations show a bad emulgation during fasted state so testosterone undecanoate is not available for incorporation into the chylomicrons. Since the digestible oleic acid ANDRIOL formulation displayed the same food effect as the non-digestible ANDRIOL TESTOCAPS formulation, the inventors anticipated that the lack of emulgation could be the main reason for the observed food effect of both formulations.

Described herein are pharmaceutical formulations comprising self-emulsifying drug delivery systems (SEDDS) comprising testosterone undecanoate, wherein the testosterone undecanoate is capable of forming a self-emulsifying system in an aqueous environment. In certain embodiments of the SEDDS described herein, are self-nanoemulsifying drug delivery systems (SNEDDS). With regard to the description below when SEDDS are discussed, SNEDDS are also contemplated. The SEDDS pharmaceutical formulations described herein have a good solvation capacity for testosterone undecanoate and are able to keep testosterone undecanoate dissolved in the gastrointestinal tract to promote contact between the oily, testosterone undecanoate containing droplets and the chylomicrons which will enter the lymphatics.

The pharmaceutical formulations described herein are designed to alter testosterone bioavailability in the fasted state which may result in less food effect. The pharmaceutical formulations described herein also allow for increased exposure of testosterone. The reduction of food effect and increased exposure may also allow for a lower dose of testosterone undecanoate compared to the ANDRIOL TESTOCAPS.

The pharmaceutical formulations described herein also demonstrate a faster onset (shorter $T_{max}$) especially in fasted state compared to the ANDRIOL TESTOCAPS. Therefore, a faster and higher extent of absorption is expected with the formulations described herein.

Specifically, described herein are self-emulsifying pharmaceutical formulations comprising testosterone undecanoate, a water soluble surfactant, a non-ionic surfactant and a water insoluble surfactant and, optionally, a digestible long-chain fatty acid ester.

Also described herein are methods for the treatment of hypogonadism comprising administering to a patient in need thereof one of the formulations described herein.

DETAILED DESCRIPTION OF THE INVENTION

Described herein are stable, liquid pharmaceutical formulations comprising testosterone undecanoate in a self-emulsifying drug delivery system (SEDDS), wherein the testosterone undecanoate is capable of forming a self-emulsifying system in an aqueous environment. In certain embodiments, the pharmaceutical formulations described herein comprise testosterone undeconoate, a water soluble surfactant, a non-ionic surfactant and a water insoluble surfactant and, optionally, a digestible long-chain fatty acid ester.

In certain embodiments, the pharmaceutical formulations described herein comprise testosterone undeconoate, a water soluble surfactant, a non-ionic surfactant and a water insoluble surfactant, and a digestible long-chain fatty acid ester. For example, in certain embodiments, the pharmaceutical formulations described herein comprise testosterone unecanoate, propylene glycol, CREMOPHOR EL, CAPRYOL 90 and ethyl oleate.

In certain embodiments, the pharmaceutical formulations described herein comprise testosterone undeconoate; a water soluble surfactant, a non-ionic surfactant and a water insoluble surfactant. For example, in certain embodiments, the pharmaceutical formulations described herein comprise testosterone unecanoate, propylene glycol, CREMOPHOR EL and CAPRYOL 90.

The formulations described herein contain between about 6% to 12% of testosterone undecanoate by weight. In certain embodiments, the formulations described herein, contain 12% or less of testosterone undecanoate by weight. In such embodiments, the amounts of testosterone undecanoate are less than that found in commercial embodiments such as ANDRIOL which contain 12% of testosterone undecanoate by weight. In certain embodiments, the formulations described herein, contain 10% or less of testosterone undecanoate by weight. In certain embodiments, the formulations described herein, contain 9% or less of testosterone undecanoate by weight. In certain embodiments, the formulations described herein, contain 7.5% or less of testosterone undecanoate by weight.

In certain embodiments, the formulations described herein contain about 12% of testosterone undecanoate. In other embodiments, the formulations described herein contain about 9% of testosterone undecanoate. In other embodiments, the formulations described herein contain about 7.5% of testosterone undecanoate. In yet other embodiments, the formulations described herein contain about 6% of testosterone undecanoate.

The formulations described herein include a water soluble (hydrophilic) surfactant, a non-ionic surfactant and a water insoluble (hydrophobic) surfactant. The surfactants can be in any ratio that will give the desired properties of the formulations with testosterone undecanoate. In certain embodiments of the formulations described herein the ratio by weight of the water soluble surfactant, a non-ionic surfactant and a water insoluble surfactant is about 1:1:1, 1:2:1, 1:3:1, 1:4:1, 1:5:1, 2:1:1, 2:2:1, 2:3:1, 2:4:1, 2:5:1, 3:1:1, 3:2:1, 3:3:1, 3:4:1, 3:5:1, 4:1:1, 4:2:1, 4:3:1, 4:4:1, 4:5:1, 5:1:1, 5:2:1, 5:3:1, 5:4:1 or 5:5:1. In certain embodiments of the formulations described herein the ratio by weight of the water soluble surfactant, a non-ionic surfactant and a water insoluble surfactant is about 1:1:2, 1:2:2, 1:3:2, 1:4:2, 1:5:2, 2:1:2, 2:2:2, 2:3:2, 2:4:2, 2:5:2, 3:1:2, 3:2:2, 3:3:2, 3:4:2, 3:5:2, 4:1:2, 4:2:2, 4:3:2, 4:4:2, 4:5:2, 5:1:2, 5:2:2, 5:3:2, 5:4:2 or 5:5:2. In certain embodiments of the formulations described herein the ratio by weight of the water soluble surfactant, a non-ionic surfactant and a water insoluble surfactant is about 1:1:3, 1:2:3, 1:3:3, 1:4:3, 1:5:3, 2:1:3, 2:2:3, 2:3:3, 2:4:3, 2:5:3, 3:1:3, 3:2:3, 3:3:3, 3:4:3, 3:5:3, 4:1:3, 4:2:3, 4:3:3, 4:4:3, 4:5:3, 5:1:3, 5:2:3, 5:3:3, 5:4:3 or 5:5:3. In certain embodiments of the formulations described herein the ratio by weight of the water soluble surfactant, a non-ionic surfactant and a water insoluble surfactant is about 1:1:4, 1:2:4, 1:3:4, 1:4:4, 1:5:4, 2:1:4, 2:2:4, 2:3:4, 2:4:4, 2:5:4, 3:1:4, 3:2:4, 3:3:4, 3:4:4, 3:5:4, 4:1:4, 4:2:4, 4:3:4, 4:4:4, 4:5:4, 5:1:4, 5:2:4, 5:3:4, 5:4:4 or 5:5:4. In certain embodiments of the formulations described herein the ratio by weight of the water soluble surfactant, a non-ionic surfactant and a water insoluble surfactant is about 1:1:5, 1:2:5, 1:3:5, 1:4:5, 1:5:5, 2:1:5, 2:2:5, 2:3:5, 2:4:5, 2:5:5, 3:1:5, 3:2:5, 3:3:5, 3:4:5, 3:5:5, 4:1:5, 4:2:5, 4:3:5, 4:4:5, 4:5:5, 5:1:5, 5:2:5, 5:3:5, 5:4:5 or 5:5:5. In certain embodiments the ratio of by weight of the water soluble surfactant, a non-ionic surfactant and a water insoluble surfactant is 1:3:5.

In the formulations described herein, at least one of the surfactants is a water soluble surfactant. Suitable water soluble surfactants include, but are not limited to, polyethylene glycol sorbitan fatty acid esters and hydrophilic transesterification products of a polyol with at least one member of the group from triglycerides; vegetable oils and hydrogenated vegetable oils such as glycerol, ethylene glycol, polyethylene glycol, sorbitol, propylene glycol, pentaerythritol, or a saccharide, d-alpha-tocopheryl polyethylene glycol 1000 succinate. In certain embodiments of the formulations described herein, the water soluble surfactant is propylene glycol.

In the formulations described herein, at least one of the surfactants is a non-ionic surfactant. Suitable non-ionic surfactants include, but are not limited to, ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates including TWEEN 80, polyoxyethylene octylphenylether, PEG-1000 cetyl ether, polyoxyethylene tridecyl ether, polypropylene glycol butyl ether, POLOXAMER 401, pluronics, stearoyl monoisopropanolamide, CREMOPHOR EL (polyethoxylated castor oil), SPAN 80 (sorbitan oleate), and polyoxyethylene hydrogenated tallow amide. In certain embodiments of the formulations described herein, the non-ionic surfactant is SPAN 80, TWEEN 80 or CREMOPHOR EL. In certain embodiments, of the formulations described herein the non-ionic surfactant is CREMOPHOR EL.

In the formulations described herein, at least one of the surfactants is a water insoluble surfactant. Suitable water insoluble surfactants include, but are not limited to, CAPRYOL 90 (propylene glycol monocaprylate), LAUROGLYCOL FFC (propylene glycol monolaurate), Propymuls (propylene glycol ricinoleate), Myverol P-06 (propylene glycol monooleate), CAPTEX 200 (propylene glycol dicaprylate/dicaprate) and CAPTEX 800 (propylene glycol dioctanoate). In certain embodiments of the formulations described herein, the water insoluble surfactant is selected from the group consisting of LAUROGLYCOL FFC and CAPRYOL 90. In certain embodiments the water insoluble surfactant is LAUROGLYCOL FFC. In certain embodiments the water insoluble surfactant is CAPRYOL 90.

In certain embodiments, the formulations described herein contain a digestible long-chain fatty acid ester. Suitable digestible long-chain fatty acid esters include, but are not limited to, glycerine trioleate and ethyl oleate. In certain embodiments, the digestible long-chain fatty acid ester is ethyl oleate.

In the formulations described herein, the long-chain fatty acid ester is present in the amount of 1% to 10% by weight. In certain embodiments, the long-chain fatty acid ester is present in the amount of 7% by weight. In certain embodiments, the long-chain fatty acid ester is present in the amount of 5% by weight. In other embodiments, the long-chain fatty acid ester is present in the amount of 3% by weight.

Certain embodiments of the formulations described herein may include a cosolvent such as TRANSCUTOL P (2-(2-ethoxyethoxy)ethanol).

Also described herein are methods for the treatment of hypogonadism comprising administering to a patient in need thereof a pharmaceutical formulations as described herein. Also described herein are uses of the formulations described herein for the treatment of hypogonadism or the manufacture of a treatment of hypogonadism.

EXAMPLES

Solubility of Testosterone Undecanoate

Solubility experiments were conducted on certain SNEDDS as well as on the individual components used in the SNEDDS. Solubility experiments were conducted on 250 µl scale and started with 25 mg testosterone undecanoate. Room temperature solid fats and most mixtures containing room temperature solid fats were stirred overnight at 40° C. All other excipients (oils, surfactants and mixtures hereof) were stirred overnight at room temperature. If visual check showed complete dissolution of testosterone undecanoate, another 25 mg of testosterone undecanoate was added and stirred to equilibrium. This step was repeated until the point of saturation was passed. The resulting suspensions were centrifuged for 6 minutes at 14.000 rpm. The supernatant was pipetted carefully from the vial and checked for visual clarity before dilution 200 to 1000 times with $H_2O$/THF (1/9 v/v). Concentration of testosterone undecanoate in the solutions was measured with HPLC. Table 1 shows the results.

TABLE 1

| Excipients and SNEDDS mixtures | Solubility (mg/ml) |
|---|---|
| Surfactants - cosolvents | |
| PROPYLENE GLYCOL | 2.1 |
| CREMOPHOR EL | 27.2 |
| POLYSORBATE 80 (TWEEN80) | 28.4 |
| TRANSCUTOL P | 57.2 |
| Non-ionic or water insoluble surfactants - cosolvent | |
| SPAN 80 | 130.4 |
| LAUROGLYCOL FFC | 175.7 |
| CAPRYOL 90 | 226.7 |
| Digestible long-chain fatty acid esters | |
| Glycerine trioleate | 60.9 |
| Ethyl oleate | 117.3 |
| Digestible oils containing long-chain fatty acids | |
| Sunflower Seed Oil | 67.3 |
| Corn Oil | 72.1 |
| Peanut Oil | 73.3 |
| Non-digestible oils | |
| Castor Oil | 103.1 |
| Non-emulsifying and non-digestible formulation | |
| ANDRIOL TESTOCAPSS formulation (Castor Oil/LAUROGLYCOL FFC (6/4) | 136.5 |
| SNEDDS - undigestible formulations | |
| Formulation A (CAPRYOL 90/TWEEN 80/TRANSCUTOL P (2:5:5)) | 56.7 |
| Formulation B (Propylene glycol/CREMOPHOR EL/CAPRYOL 90 (1:3:5)) | 104.7 |

TABLE 1-continued

| Excipients and SNEDDS mixtures | Solubility (mg/ml) |
|---|---|
| SNEDDS formulations with digestible component | |
| Formulation C (Sunflower Seed Oil/CREMOPHOR EL/SPAN 80 (3/4/3 w/w/w)) | 57.5 |
| Formulation D (Corn Oil/CREMOPHOR EL/SPAN 80 (3/4/3 w/w/w)) | 58.9 |
| Formulation E (Sunflower Seed Oil/CREMOPHOR EL/Maisine (1:1:1)) | 66.0 |

As you can see Formulation B is the closest to the ANDRIOL TESTOCAPS formulation for solubilizing testosterone undecanoate.

Homogeneity of Formulations

The formulations containing testosterone undecanoate should stay clear and homogeneous. For this purpose testosterone undecanoate has been dissolved in selected formulations. The amount of testosterone undecanoate added to the SNEDDS depends on the maximum solubility. To test the stability of the formulations in terms of homogeneity during storage, 1 ml of each of the formulations listed in Table 2 was put into a glass vial, closed under $N_2$ and kept at room temperature for 4 weeks. After 4 weeks the visual appearance was noted. All tested formulations stayed homogeneous upon visual inspection after 4 weeks. In two formulations, Formulation C and Formulation G some glass-like crystals appeared within 4 weeks. These crystals were crystallized testosterone undecanoate, indicating the amount of dissolved testosterone undecanoate was close to the maximum solubility.

TABLE 2

| Formulation | Amount of Testosterone Undecanoate (%) | >4 weeks standing at room temperature |
|---|---|---|
| Formulation B | 9 | Clear |
| Formulation C | 6 | Some glass-like crystals on bottom |
| Formulation D | 6 | Clear |
| Formulation F (Propylene glycol/Cremophor RH40/Capryol 90 (1:3:5)) | 9 | Clear |
| Formulation G (Formulation B + 5% EtOH (w/w) | 12 | Some glass-like crystals on bottom |
| Formulation H (Formulation B + 5% ethyl oleate (w/w) | 12 | Clear |

Emulsification of Formulations

For determination of the self-emulsifying properties of the selected formulations in watery systems, two methods were used. The first method was slow titration of the oily mixture with aqueous (Method 1). The second method was addition of the oily mixture to the aqueous phase (Method 2).

Method 1: Slow titration of oily mixture with aqueous phase. Water was added in portions to 250 µl SNEDDS in a glass vial with a magnetic stirrer bar, starting with 50 µl portions and ending with a 10 ml portion. After addition of each portion the mixture was stirred until no more changes in constitution were seen. The constitution was noted and another portion of water was added. These steps were repeated to a volume of 15 ml. Then 1 ml was taken and added to 4 ml of stirring water. The resulting solution was stirred at least 2 h before visual appearance was noted.

Method 2: Addition of oily mixture to aqueous phase. 25 µl SNEDDS was added to 6.25 ml stirred water. If the emulsion was not formed within one minute vortexing was used to mix the two phases. After mixing the solution was stirred for at least 2 h before the visual appearance was noted and/or the droplet size was measured.

Dilution of both methods was chosen to lead to a concentration of approx. 1 ml SNEDDS in 250 ml water, the amount of water stands for the stomach-volume. Several SNEDDS were emulgated via Method 1 as well as Method 2 to compare the resulting emulsions. The formulations which are emulgated contain 6%, 9% or 12% testosterone undecanoate. This depends on the maximum solubility. 12% matches the testosterone undecanoate concentration in ANDRIOL TESTOCAPSS.

To score the self-emulsifying properties of the formulations, the visual appearance of the emulsions were noted in Table 3. A milky appearance of the emulsion indicated a larger droplet size; a slightly milky, milky haze, haze, bluish transparent or clear appearance indicates possible formation of a nano-emulsion. Droplet size parameters of the emulsions in the range of slightly milky to clear are measured with Dynamic Light Scattering techniques.

TABLE 3

| Formulation | Amount of Testosterone Undecanoate (%) | Method | Visual appearance after 16 hrs of stirring |
|---|---|---|---|
| Formulation B | 9 | 1 | Haze |
| Formulation C | 6 | 1 | Bluish transparent |

TABLE 3-continued

| Formulation | Amount of Testosterone Undecanoate (%) | Method | Visual appearance after 16 hrs of stirring |
|---|---|---|---|
| Formulation D | 6 | 1 | Bluish transparent |
| Formulation F (Propylene glycol/Cremophor RH40/Capryol 90 (1:3:5)) | 9 | 1 | Light milky |
| Formulation G (Formulation B + 5% EtOH (w/w)) | 12 | 2 | Haze |
| Formulation H (Formulation B + 5% ethyl oleate (w/w)) | 12 | 2 | Milky haze |

Droplet Size Measurements

Droplet sizes were obtained with Dynamic Light Scattering (DLS) techniques. These measurements were performed to get more insight in the droplet size and droplet size distribution of the droplets in the emulsions obtained via Method 1 or 2. Measurements were performed with a Malvern DLS Nanosizer or Zetasizer Nano ZS. Approximately 1 ml of the emulsion was pipetted into a low volume disposable sizing cuvette, checked for absence of air-bubbles and placed in the cuvet holder. Results are shown in Table 4.

TABLE 4

| Formulation | Amount of Testosterone Undecanoate (%) | Method | Total Average diameter (nm) | PdI (polydispersity index) | Average diameter peak 1 (nm) | Volume Peak 1 (%) |
|---|---|---|---|---|---|---|
| Formulation B | 9 | 1 | 68.5 | 0.15 | 54.6 | 100 |
| Formulation C | 6 | 1 | 41.5 | 0.4 | 20.4 | 100 |
| Formulation D | 6 | 1 | 27.9 | 0.21 | 16.9 | 100 |
| Formulation F (Propylene glycol/Cremophor RH40/Capryol 90 (1:3:5)) | 9 | 1 | 142.1 | 0.14 | 154.6 | 100 |
| Formulation G (Formulation B + 5% EtOH (w/w)) | 12 | 2 | 55.7 | 0.18 | 44.0 | 99 |
| Formulation H (Formulation B + 5% ethyl oleate (w/w)) | 12 | 2 | 69.6 | 0.22 | 56.0 | 97 |

Animal Study

Formulations Used in Animal Studies

Capsules were made with the formulations shown in Table 5. The liquid excipients were weighed and mixed. Subsequently, the testosterone undecanoate was added, and the mixtures were placed on a rollerbank for a period between 1 and 3 days. Table 6 shows the amount of formulation and testosterone undecanoate per capsule.

TABLE 5

| Formulation | Testosterone Undecanoate (%) | Propylene glycol (mg) | Cremophor EL (mg) | Capryol 90 (mg) | 5% ethyl oleate | Testosterone Undecanoate (mg) | Total |
|---|---|---|---|---|---|---|---|
| Formulation B0 | 0 | 116.5 | 354.1 | 529.5 | — | — | 1000 |

TABLE 5-continued

| Formulation | Testosterone Undecanoate (%) | Propylene glycol (mg) | Cremophor EL (mg) | Capryol 90 (mg) | 5% ethyl oleate | Testosterone Undecanoate (mg) | Total |
|---|---|---|---|---|---|---|---|
| Formulation B | 9 | 106.0 | 322.2 | 481.8 | — | 90.0 | 1000 |
| Formulation B1 | 7.5 | 107.7 | 327.5 | 489.7 | — | 75.0 | 1000 |
| Formulation H0 | 0 | 110.6 | 336.4 | 503.0 | 50.0 | — | 1000 |
| Formulation H1 | 9 | 100.7 | 306.1 | 457.7 | 45.5 | 90.0 | 1000 |
| Formulation H2 | 7.5 | 102.3 | 311.2 | 465.3 | 46.3 | 75.0 | 1000 |

TABLE 6

| Formulation | Testosterone Undecanoate (%) | Amount of Mixture per capsule (mg) | Amount of Testosterone Undecanoate per capsule (mg) |
|---|---|---|---|
| Formulation B0 | 0 | 444.44 | 0 |
| Formulation B | 9 | 444.44 | 40 |
| Formulation B1 | 7.5 | 533.33 | 40 |
| Formulation H0 | 0 | 444.44 | 0 |
| Formulation H1 | 9 | 444.44 | 40 |
| Formulation H2 | 7.5 | 533.33 | 40 |

To estimate the emulsification behavior of the formulations in the gastro-intestinal (GI) tract, the capsules in Table 6 were diluted with different amounts of water or Simulated Gastric Fluid (SGF). A single capsule was added to a volume of 250, 60, or 30 mL to mimic a range of gastric volumes in man and dog. Visual appearance and droplet sizes were determined. For all formulations a bluish transparent emulsion was observed for capsules added to 250 mL of liquid. For all formulations a bluish transparent emulsion with a slight white haze was observed for capsules added to 60 mL of liquid. For all formulations a milky white haze was observed for capsules added to 30 mL of liquid. Droplet size of the nano-emulsions were also measured and shown below in Table 7.

After 6 weeks of storage at 5° C./ambient humidity, 25° C./60% RH or 40° C./75% RH the emulsions in 60 mL of SGF had a bluish white haze. Droplet size of emulsions made from capsules that were stored for 6 weeks at different conditions are shown in Table 8.

TABLE 7

| | | Volume peak 1 (and 2 in parentheses) in d · nm | | | | | |
|---|---|---|---|---|---|---|---|
| | | 250 mL | | 60 mL | | 30 mL | |
| Formulation B0 (0% TU) | Water | 118.6 | 86.1 | 49.5 | 51.0 | 56.5 | 48.6 (201.2) |
| | SGF | 92.7 (303.0) | 93.4 (334.7) | 53.7 | 55.5 | 67.4 (348.2) | 69.7 (357.2) |
| Formulation B (9% TU) | Water | 80.4 | n.d. | 52.2 | n.d. | 62.9 | n.d. |
| | SGF | 96.5 | n.d. | 64.0 | n.d. | 204.5 (49.2) | n.d. |
| Formulation B1 (7.5% TU) | Water | 94.9 | 100.3 | 63.4 | 57.0 | 156.5 (1331.0) | 68.4 |
| | SGF | 146.5 | 212.6 | 97.7 | 75.4 | 240.8 | 234.0 (58.3) |
| Formulation H0 (0% TU) | Water | 69.9 | 102.5 | 50.1 | 51.6 | 64.3 | 56.8 |
| | SGF | 133.5 | 86.8 (207.9) | 53.6 | 54.6 | 71.1 | 57.1 (283.7) |
| Formulation H1 (9% TU) | Water | 64.2 | n.d. | 59.2 | n.d. | 82.2 | n.d. |
| | SGF | 82.1 | n.d. | 63.7 | n.d. | 126.6 | n.d. |
| Formulation H2 (7.5% TU) | Water | 78.3 | 89.3 | 63.2 | 57.6 | 113.0 | 67.6 |
| | SGF | 99.0 | 105.8 | 67.3 | 67.7 | 69.5 (223.8) | 187.3 (51.5) |

All formulations form the best emulsion when emulsified in 60 mL water or SGF. Little variability is observed between water and SGF. All formulations seem to emulsify equally well in 60 mL of medium. For 250 and 30 mL, the emulsions seem coarser, and sometimes more than one peak is observed. For these volumes, the results are better in water than in SGF. The formulations comprising ethyl oleate seem to form a better emulsion in these volumes than the formulations without ethyl oleate. Considering that the 1/60 dilution is used to predict the in-vivo behavior in fasted state man since this mimics the ratio in human fasted state stomach, it is expected that all formulations form nanoemulsions in the fasted human gastro-intestinal tract.

TABLE 8

Volume peak 1 (and 2 in parentheses) in d · nm

| Formulation | T = 0 (emulsions in 250 mL water) | T = 6 weeks (emulsion in 60 mL SGF) | | |
|---|---|---|---|---|
| | | 5° C./amb | 25° C./ 60% RH | 40° C./ 75% RH |
| Formulaton B0 (0% TU) | 37.0 | 54.1 | 53.4 | 55.3 |
| Formulaton B (9% TU) | 55.6 | 75.9 | 73.0 (703.7 (8%)) | 70.8 |
| Formulaton B1 (7.5% TU) | 56.4 | 64.6 | 64.4 | 65.0 |
| Formulaton H0 (0% TU) | 44.1 | 54.7 | 65.1 | 54.5 |
| Formulaton H (9% TU) | 55.0 | 67.7 | 67.9 | 67.3 |
| Formulaton H1 (7.5% TU) | 39.3 | 64.3 | 64.7 | 63.9 |

For almost all formulations and all conditions, nanoemulsions were formed. (<100 nm). No large difference was observed between the different storage temperatures, indicating that the same droplet sizes can be obtained after storage.

Crystallization tendency was also measured in the capsule formulations. All formulations remained clear at 3 hours and 96 hours when stored at 7° C. Formulations were also exposed to a freeze-thaw cycle of 3 hours at −80° C., then 1 hour at room temperature, then 96 hours at −80° C. and finally 2 hours at room temperature. All formulations except Formulation B were solid at −80° C. and clear at room temperature. Formulation B was clear at room temperature with some tiny needles present but after shaking was clear within a few hours.

Degradation products of the capsules were determined directly after manufacturing of the capsules and after storage during six weeks at 5° C./ambient humidity, 25° C./60% RH, and 40° C./75% RH. The results show that the stability of the different formulations was similar. Some degradation products were formed after storage at 40° C./75% RH during six weeks and the above formulations are expected to have a shelf-life of about 9 months at 2-25° C.

In Vivo Study

An in vivo study was performed. Twelve female Beagle dogs with body weight range 7.44-12.9 kg, aged 1-2 years at dosing were assigned to three different dosing groups and administered test formulations according to the scheme shown in Table 5.

TABLE 5

| Week | Group No. | Pre-Dose Fast/Fed | Dose of Testosterone Undecanoate | Formulation |
|---|---|---|---|---|
| 1 | 1 | Fasted | 40 mg | Formula B with 9% Testosterone Undecanoate |
| | 2 | Fed | 40 mg | Formula H with 9% Testosterone Undecanoate |
| | 3 | Fasted | 40 mg | ANDRIOL TESTOCAPSS |
| 2 | 1 | Fed | 40 mg | Formula B with 9% Testosterone Undecanoate |
| | 2 | Fasted | 40 mg | Formula H with 9% Testosterone Undecanoate |
| | 3 | Fed | 40 mg | ANDRIOL TESTOCAPSS |
| 3 | 1 | Fasted | 40 mg | Formula B with 9% Testosterone Undecanoate |
| | 2 | Fed | 40 mg | Formula H with 9% Testosterone Undecanoate |
| | 3 | Fasted | 40 mg | ANDRIOL TESTOCAPSS |

For testosterone, the mean $AUG_{0-12\ hr}$ were 23.5 and 33.8 nM*hr for Formula B and Formula H, respectively, in fasted dogs compared to 9.57 nM*hr for ANDRIOL TESTOCAPS. The mean $AUC_{0-12\ hr}$ increased to 90.8 and 123 nM*hr for Formula B and Formula H, respectively, in dogs when dosing with high fat meal compared to 50.6 nM*hr for ANDRIOL TESTOCAPS. The mean $C_{max}$ were 11.9 and 18.5 nM for Formula B and Formula H, respectively, in fasted dogs compared to 4.89 nM for ANDRIOL TESTOCAPS. The mean $C_{max}$ increased to 42.3 and 57.9 nM for Formula B and Formula H, respectively, in dogs when dosing with high fat meal compared to 18.2 nM for ANDRIOL TESTOCAPS. In addition, the median $T_{max}$ increased from 1.5, 1.2, 2.2 hr in fasted state to 3.0, 3.0 and 4.0 hr for Formula B, Formula H and ANDRIOL TESTOCAPS, respectively, when dosing with high fat meal.

For testosterone undecanoate (TU), the mean $AUG_{0-12\ hr}$ were 205 and 423 nM*hr for Formula B and Formula H, respectively, in fasted dogs compared to 89.1 nM*hr for ANDRIOL TESTOCAPS. The mean $AUC_{0-12\ hr}$ increased to 1660 and 2300 nM*hr for Formula B and Formula H, respectively, in dogs when dosing with high fat meal compared to 1130 nM*hr for ANDRIOL TESTOCAPS. The mean $C_{max}$ were 144 and 311 nM for Formula B and Formula H, respectively, in fasted dogs compared to 55.6 nM for ANDRIOL TESTOCAPS. The mean $C_{max}$ increased to 1090 and 1550 nM for Formula B and Formula H, respectively, in dogs when dosing with high fat meal compared to 512 nM for ANDRIOL TESTOCAPS. In addition, the median $T_{max}$ slightly increased from 1.5, 1.5, 2.5 hr in fasted state to 2.5, 2.5 and 3.0 hr for Formula B, Formula H and ANDRIOL TESTOCAPS, respectively, when dosing with high fat meal.

The $AUC_{0-12\ hr}$ ratios of testosterone for tested formulations in fed versus fasted state were 3.86, 3.64 and 5.29 for Formula B, Formula H and ANDRIOL TESTOCAPS, respectively. The $AUC_{0-12\ hr}$ ratios of testosterone undecanoate for tested formulations in fed versus fasted state were 8.10, 5.44 and 12.7 for Formula B, Formula H and ANDRIOL TESTOCAPS, respectively. Although significant food effect would still be expected for tested formulations, the tested formulations showed decreased exposure ratio between fed and fasted state than ANDRIOL TESTOCAPS.

When looking into the $AUC_{0-12\ hr}$ ratios of testosterone for tested formulation versus ANDRIOL TESTOCAPS in fed state, the $AUC_{0-12\ hr}$ ratios of testosterone for tested formulations versus ANDRIOL TESTOCAPS when dosing with high fat meal were 1.79 and 2.43 for Formula B and Formula H, respectively. While in fasted state, the increase of exposure extended to 2.46-fold and 3.53-fold for Formula B and Formula H, respectively. For testosterone undecanoate, the $AUC_{0-12\ hr}$ ratios for tested formulations versus ANDRIOL TESTOCAPS when dosing with high fat meal were 1.47 and 2.04 for Formula B and Formula H, respectively. While in fasted state, the increase of exposure extended to 2.30-fold and 4.75-fold for Formula B and Formula H, respectively.

In summary, based on the results of this dog study, food effect is still observed for tested formulations. However, the tested formulations showed significant increase of exposure than the ANDRIOL TESTOCAPS (average ~2× in fed state and ~3.5× in fasted state for testosterone undecanoate). A decreased exposure ratio between fed and fasted state than ANDRIOL TESTOCAPS was observed for tested formulations.

What is claimed is:

1. A pharmaceutical formulation comprising: testosterone undecanoate; a compound selected from the group consisting of glycerol, ethylene glycol, polyethylene glycol, sorbitol and propylene glycol; a non-ionic surfactant and a water insoluble surfactant, wherein the glycerol, ethylene glycol, polyethylene glycol, sorbitol or propylene glycol; the non-ionic surfactant and the water insoluble surfactant are present in a weight ratio of 1:3:5; and a digestible long-chain fatty acid ester.

2. The pharmaceutical formulation of claim 1, wherein the water soluble surfactant is propylene glycol.

3. The pharmaceutical formulation of claim 1, wherein the water insoluble surfactant is selected from the group consisting of propylene glycol monocaprylate, propylene glycol monolaurate, propylene glycol ricinoleate, propylene glycol monooleate, propylene glycol dicaprylate/dicaprate and propylene glycol dioctanoate).

4. The pharmaceutical formulation of claim 1, wherein the water insoluble surfactant is propylene glycol monocaprylate.

5. The pharmaceutical formulation of claim 1, wherein the non-ionic surfactant is selected from the group consisting of sorbitan monooleate, polysorbate 80 and polyethoxylated castor oil.

6. The pharmaceutical formulation of claim 1, wherein the non-ionic surfactant is polyethoxylated castor oil.

7. The pharmaceutical formulation of claim 1, wherein the digestible long-chain fatty acid ester is selected from the group consisting of glycerine trioleate and ethyl oleate.

8. The pharmaceutical formulation of claim 1, wherein the digestible long-chain fatty acid ester is ethyl oleate.

9. The pharmaceutical formulation of claim 1, wherein the amount of the digestible long-chain fatty acid ester is about 5% by weight.

10. The pharmaceutical formulation of claim 1, wherein the amount of testosterone undecanoate is about 6% to 12% by weight.

11. The pharmaceutical formulation of claim 1, wherein the amount of testosterone undecanoate is less than 10% by weight.

12. A pharmaceutical formulation consisting essentially of: testosterone undecanoate; glycerol, ethylene glycol, polyethylene glycol, sorbitol and propylene glycol; a non-ionic surfactant; a water insoluble surfactant and a digestible long-chain fatty acid ester, wherein the glycerol, ethylene glycol, polyethylene glycol, sorbitol or propylene glycol; the non-ionic surfactant and the water insoluble surfactant are present in a weight ratio of 1:3:5.

13. A method of treating hypogonadism in a patient in need thereof, comprising administering to the patient the pharmaceutical formulation of claim 1.

* * * * *